United States Patent [19]

Stordahl

[11] Patent Number: 5,040,984

[45] Date of Patent: Aug. 20, 1991

[54] DENTAL IMPLANT

[76] Inventor: Finn R. Stordahl, 8914 N. Sun Lakes Blvd., Sun Lakes, Ariz. 85248

[21] Appl. No.: 134,255

[22] Filed: Dec. 17, 1987

[51] Int. Cl.⁵ .............................................. A61C 8/00
[52] U.S. Cl. .................................................... 433/173
[58] Field of Search ................ 433/173, 174, 175, 176

[56] References Cited

U.S. PATENT DOCUMENTS 2,258,207 10/1941 Irwin ..................................... 433/173
3,738,008 6/1973 Edelman ............................ 433/176
4,220,712 9/1980 Staffolani ............................ 433/173
4,253,833 3/1981 Edelman ............................. 433/173

Primary Examiner—John J. Wilson

[57] ABSTRACT

A dental implant for permanently mounting in the mouth having a connected base and top. The base has at least two flanges one of which is integral with the bottom of the base and the other is rotatably mounted on the bottom of the base. The rotatable flange automatically rotates outwardly as the implant is inserted to hold the implant in the jaw bone.

3 Claims, 4 Drawing Sheets

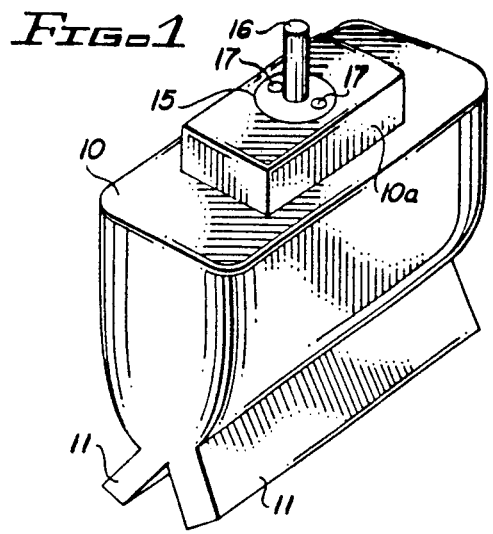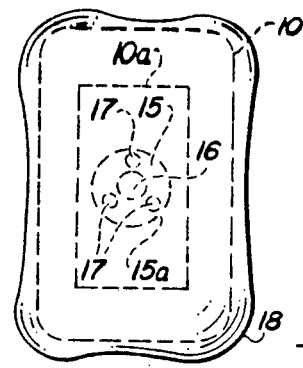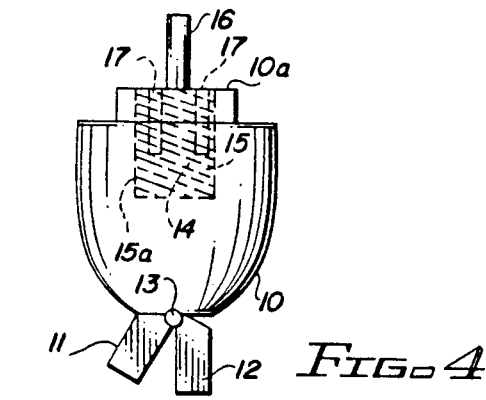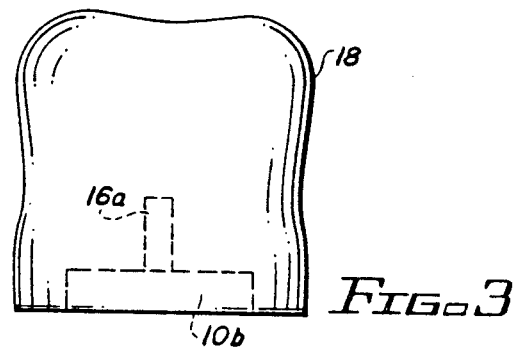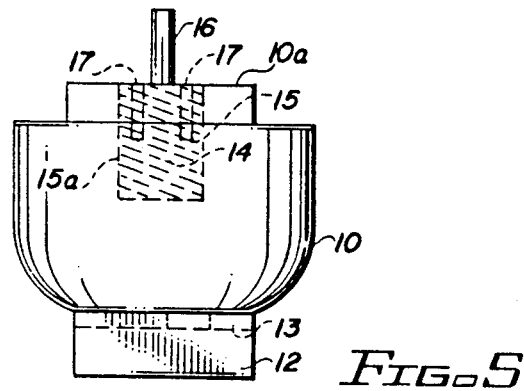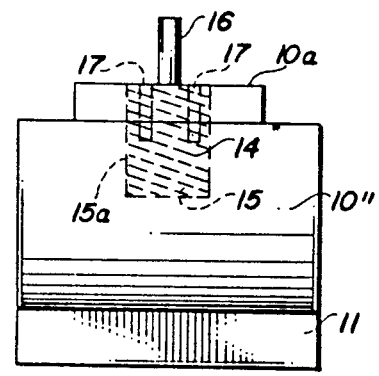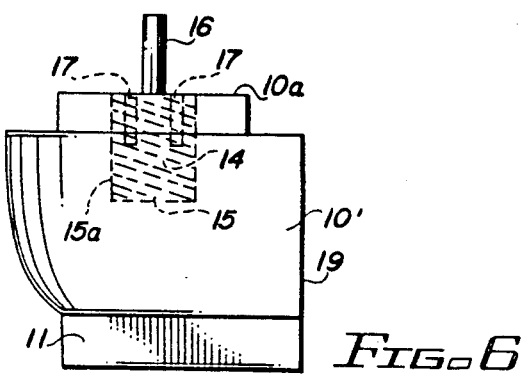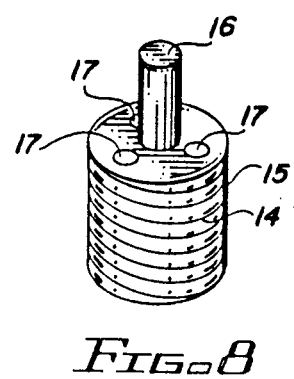

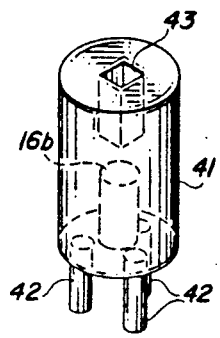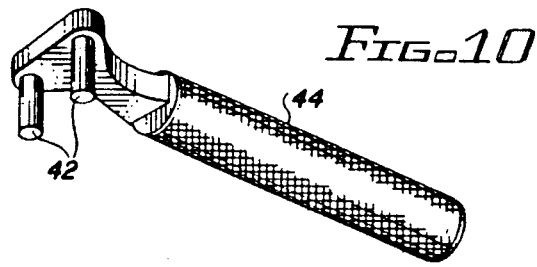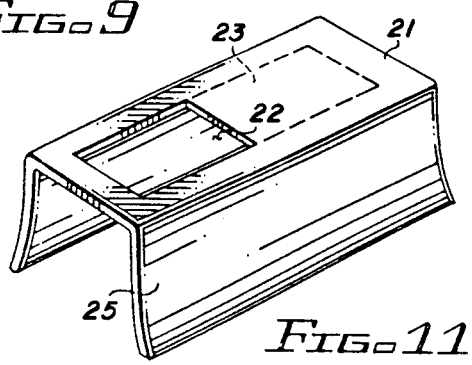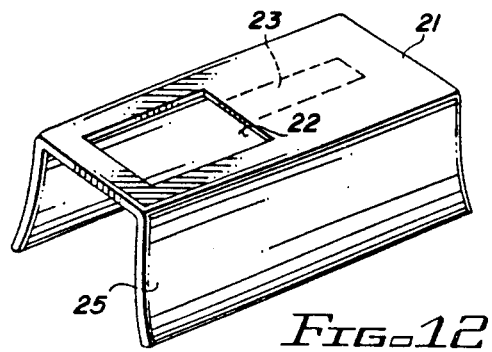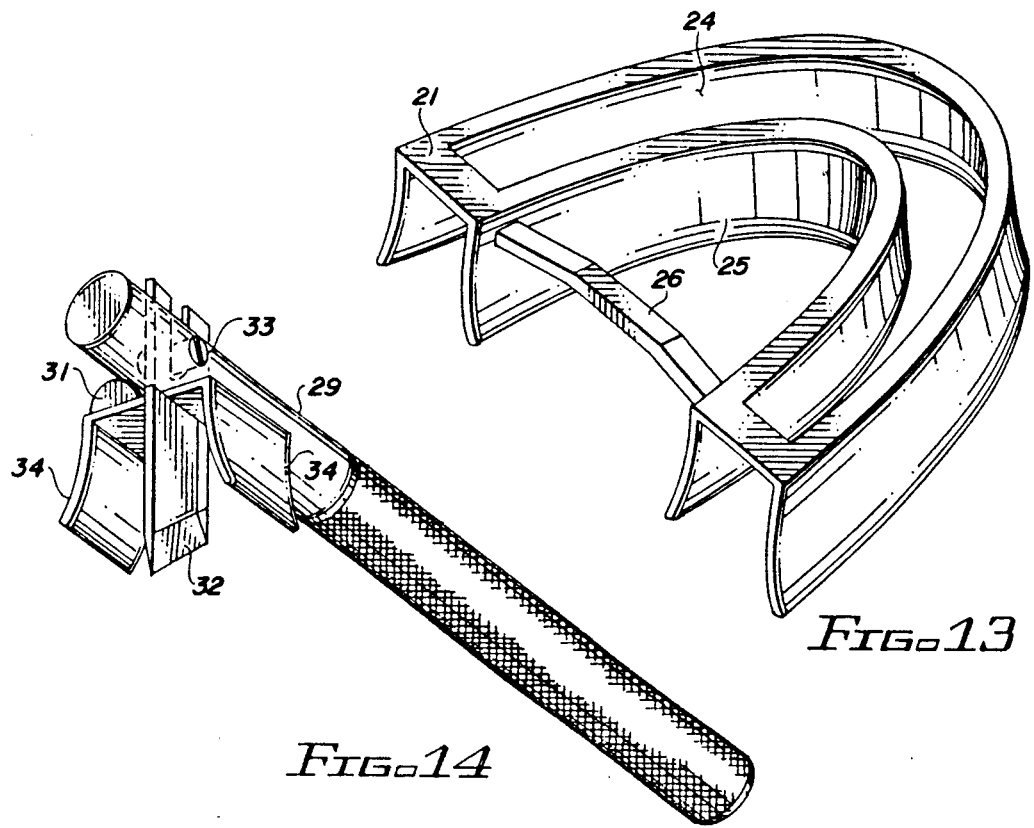

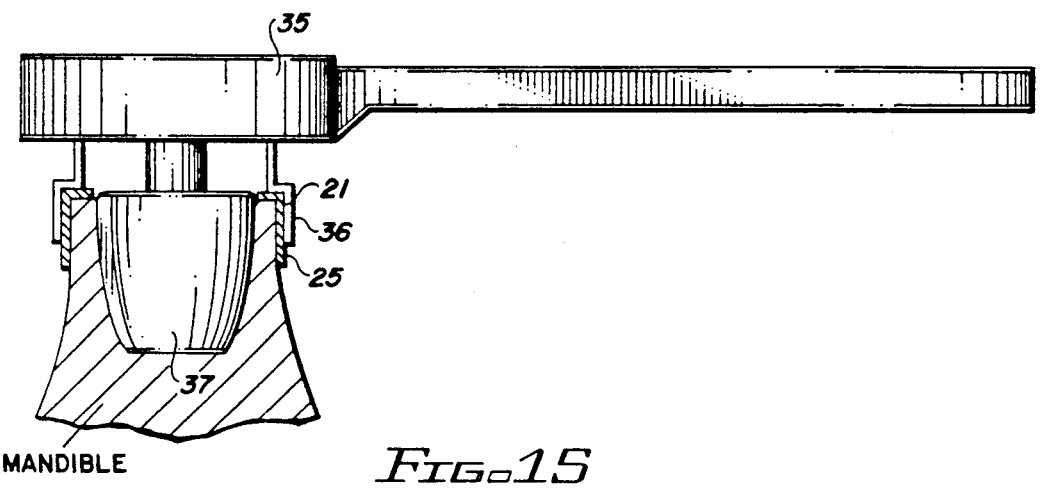
MANDIBLE  FIG. 15
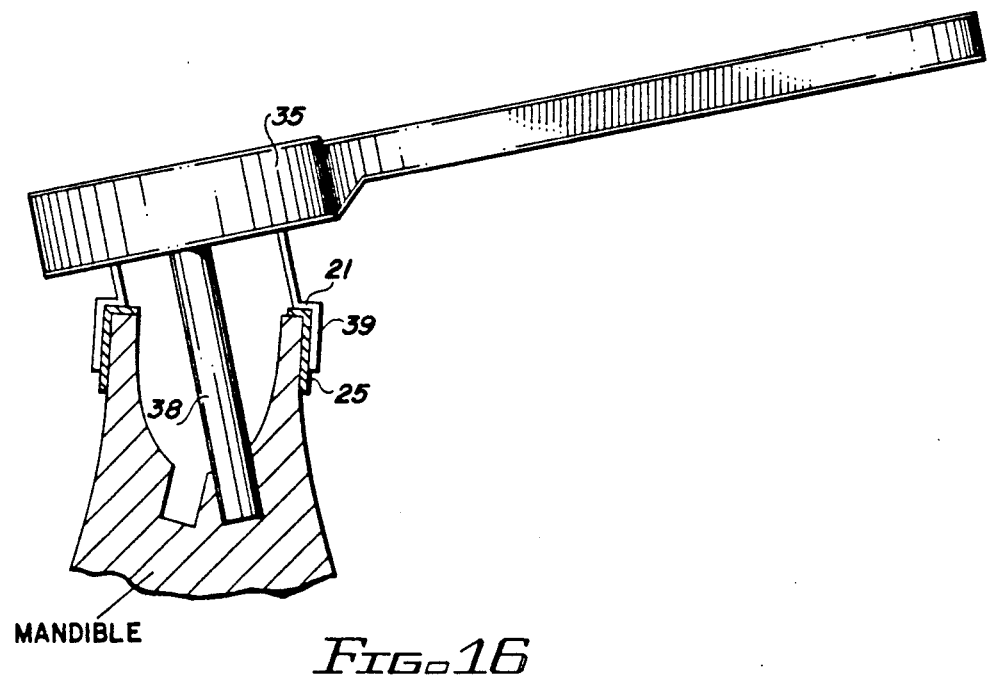
MANDIBLE  FIG. 16

DENTAL IMPLANT

BACKGROUND OF THE INVENTION

The present invention relates to dental endosteal implants, with devices to aid in the placement of the implant, and procedures for placing the implant.

In recent years, dental endostral implants have been implanted through the tissue of the aveolar ridge into the jaw bone. Such implants are described in several patents and the publications cited therein, particularly U.S. Pat. Nos. 4,293,302; 4,220,712; 4,079,515 and 3,849,887. If properly placed, these implants are eventually affixed by bone ingrowth with the aid of serrated or porous portions within the implant.

In all noted cases the implant is placed into a straight or possibly tapered hole which is drilled into the jaw bone or in the root opening left when a tooth is extracted. This technique has the disadvantages of the jawbone being too soft to stabilize the implant, or the implant becoming loosened prior to the formation of bone ingrowth to "lock" the implant into the jaw.

In U.S. Pat. No. 4,220,712, and improvement to this technique utilizes spreadable metal tips which are driven into the jawbone to stabilize the implant. However, the force necessary to drive the tips into the bone may cause the bone to crack.

Once that implanted portion is stabilized in the jaw bone by ingrowth and the attachment of periodontal ligaments to the implant, an artificial crown is secured to the protruding stem of the implant, usually through the use of an epoxy resin. In U.S. Pat. No. 4,220,712, the implanted stem is made in two pieces such that the protruding stem is screwed into the lower implanted portion. The cap is then applied using an epoxy.

OBJECTS AND SUMMARY OF THE INVENTION

It is the object of the invention to provide a dental implant which is more stable in the jaw bone than previously utilized implants.

It is the further object to provide an implant which better distributes the forces encountered in chewing, thus reducing the chance of damage to the normal bone structure.

It is also an object of the invention to provide tools and fixtures for placing the implant of the present invention.

It is still further and object of the invention to provide a new and unique method for placing a dental implant.

The invention includes an implant composed of several parts including a base, a replaceable stem and a cap. The base has at its lower end two flanges, with the options of at least one of the flanges being moveable, or both flanges remaining stationary. The upper end of the base has a threaded hole therein which is mated to the threaded bottom of the stem.

The flange arrangement is designed to produce an implant of increased stability when compared to prior devices. The invention includes base structures suitable for single implants and caps or multiple adjoining capped base implants.

Since the implant of the invention is different in structure from the prior art implants, different techniques must be used to prepare the jaw for receiving the implant. To aid the dental surgeon in preparing the jaw bone, several unique tools and fixtures are required. These include router jigs, a gum cutting scalpel, router bits, and a stem tightening socket and a wrench.

BRIEF DESCRIPTION OF THE DRAWINGS

FIG. 1 is a partial front and top view to give an overall view of the implant base.

FIG. 2 is a top view of a cap which fits the base,

FIG. 3 is a front partial cutaway view of a base and stem combination of a dental implant on which the cap shown in FIG. 2 fits according to the present invention;

FIG. 4 is a side view of the cap of FIG. 2.

FIG. 4 is a side view of the cap of FIG. 5;

FIG. 6 is a side view of the end base structure useful in a multiple base application;

FIG. 7 is a side view of a base portion utilized between end base structures in a multiple base application;

FIG. 8 is a perspective view of the replaceable stem of FIGS. 1, 3, 5, 6 and 7;

FIGS. 9, 10, and 11 are scalpel and router jigs, shown in perspective, used for cutting the gum and routing the jaw bone in single, adjoining and full denture replacement proceedures according to the present invention;

FIG. 12 is a perspective view of a gum cutting scalpel which can be used in conjunction with the jigs of FIGS. 9, 10 or 11;

FIGS. 13 and 14 are side views of the router, guide, and bit utilized to drill the central implant dado groove and the angled dado grooves to accomodate the base flanges;

FIG. 15 is a perspective view taken from inside the mouth, showing the implanted caps and temporary holding wires and strips;

FIG. 16 is a top perspective view showing the socket used to install or remove the replaceable stem of FIG. 8.

DETAILED DESCRIPTION OF THE INVENTION

Figure 17:
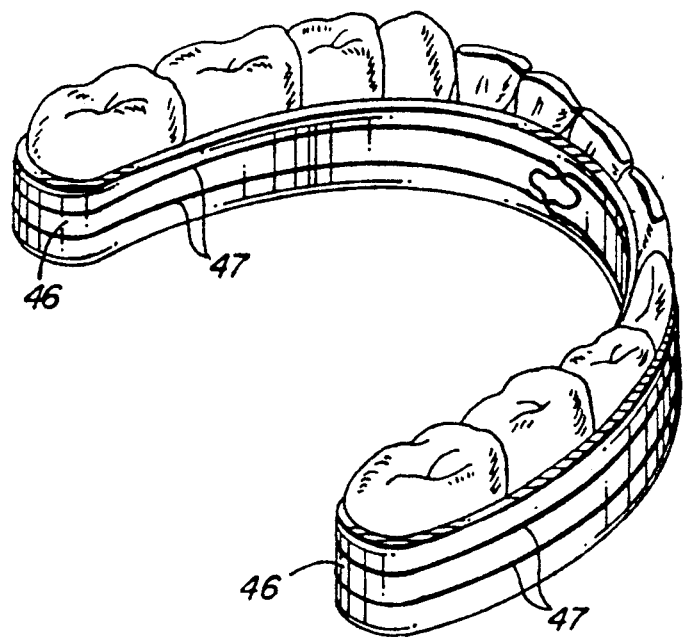
FIG. 17 is a top view of a wrench to install or remove the replaceable stem of FIG. 8.

The first embodiment of the invention, shown in FIGS. 2 and 5, is a single base structive 10, which will utilize its shape to stabilize the implant. The lower end of the base 10, which is implanted into the jaw bone, has in the preffered embodiment, at least one stationary flange 11 and the option of at least one moveable flange 12. The moveable flange 12 may be attached to the bottom of the base 10 by a hinge arrangement 13 or other suitable structure which allows it to be rotated from its closed position for insertion (the dotted position in FIG. 3) to the open, implanted position as shown in solid lines.

In this invention, an immediate tooth replacement can take effect, where both flanges 11 are fixed on the base 10 and the cap 18 completely installed on the base 10. However, it is not necessary that flanges normally be fixed, as one, or both may be designed to rotate. The top of the base 10 has a threaded hole 14 therein to accept a stem 15, the stem having a precisely matched thread pattern 14. The base 10 is composed of biocompatible materials currently utilized by the trade for similar dental applications FIG. 8 shows the repacement stem 15, which is placed in the base 10 as shown in FIGS. 3, 5, 6 and 7. The stem is threaded (14) so that it can be removed from the base 10 if needed. At the top of the stem 15 is a post 16, preferably tapered and fluted so that a cap 18 can easily be placed thereon and and readily adhered thereto using quality glues or epoxy resins. The fluting helps to lock the cap 18 to the post 16 once the adhesive takes effect. It is contemplated that other mechanical means can be used to secure the cap 18 to the post 16. The stem 15 also has at least two holes 17 located in the top thereof for use in tightening the stem 15 into, or removing the stem 15 from the base 10.

FIGS. 2 and 4 show the cap 18 used in the replacement of a molar. Within the cap 18 are indentations 10b and 16a of sizes to closely match the straight sided rectangular ridge 10a and post 16 over which it will be placed. Other caps 18 which are to replace other teeth will have a similar internal structure.

The basically rectangular shaped cap 18 is sized so that the length is equal to the base 10, and is sized as in FIG. 2 so that there is enough width to overlay the edges of the primary dado cut as in FIG. 13, for added strength during the masticating process. The extra cap width will permit the gum to return to its normal position, on a parallel with the jaw bone, and above the bottom of cap 18, for both hygenic benefit and cosmetic appearance.

FIGS. 6 and 7 show a second embodiment of the base 10 wherein several adjacent implants are to be placed into the bone. The base 10' of FIG. 6, used on the end(s) in a multiple base application, and has an adjacent edge 19 which conforms to a mating edge 20 of a center base 10''. While it is desired that the adjacent bases be in contact with each other, to give added structural rigidity they may be spaced from each other or, in the alternative, made to interlock with each other. A similar but mirror image to base 10' would be used on the other end of the multiple base, or base 10' could be reversed so that the adjacent edges 19 could butt upon each other for a dual implant. The base structures 10' and 10'' utilize the same design stem 15 and cap 18 as the earlier described embodiment.

FIGS. 9, 10 and 11 show jigs which are used as a guide for a gum cutting scalpel and a mandible/maxilla router. Depending on the number and size of teeth to be implanted, several jigs 21 may be required. For example, FIG. 9 shows a jig 21 for a single large tooth, such as a molar. If two adjacent teeth of the same size are to be implanted, the area 23 enclosed by dotted lines would be open. A reduced adjacent cutout 24 would be used where two teeth of dissimilar size are to be implanted, such as a canine tooth next to a molar. In use the jig 21 is placed over the area of the gum to be operated upon with a skirt 25 placed on both sides of the aveolar ridge. While the jig 21 shown is linear in structure it is contemplated that the jig could also be curved to better fit the natural curve of the gum line. This is shown in FIG. 11 which shows a jig 21 utilized for a full denture replacement or when several implants are to be made in the same jaw but natural teeth are to left undisturbed.

FIG. 12 shows the gum cutting scalpel 29 utilized in conjunction with the jig 21 in the implant procedure, consisting of a handle 30 with a scalpel guide 31 and cutting blade 32 mounted on the end thereof by threaded connectors 33. To cut the center line of the gum the scalpel guide 31 rests on the upper surface of the jig 21 with the wing 34 riding along the jig skirt 25. With the guide and wing, 31 and 34 removed, the blade can be used to peel away the gum from the maxilla and or mandible.

FIGS. 13 and 14 depict the utilization of router 35 hollowing out the jaw bone to receive the implant. The router 35 can be either electrically or fluid driven, as is common in the dental or orthopedic arts for forming holes in bone. The under surface of the router is modified to receive a jig riding guide 36. In use, the guide 36 rests on top of the jig 21. A bit 37 is sized and attached to the router 35 in such a manner that the router 35, guide 36 and jig 21 interact to closely control the depth of the cut into the mandible and/or maxilla at the various locations of molars, canines and incisors. While different shaped router bits may be utilized, the router bit 37 shown in FIG. 13 is preferably shaped to produce a dado cut which results in enabling a precise implant shape to absorb the preferred balanced over-all pressure more thoroughly between the implant base 10 and the jaw bone during mastication.

FIG. 14 shows a router bit 38 for forming straight dado cuts 40 into which the flanges 11 and/or 12 are placed. The precise angle at which the flange depressions are routed is controlled by replacing jig over-riding guide 36 by a guide 39 which provides the necessary offset to create the dado cut 40. To produce the precise opposite angle cut 40, the guide 39 is reversed.

The socket 41 of FIG. 15 is for use to tightly insert the replaceable stem 15 into the base 10. The socket 41, preferably composed of a high strength metal, has pegs 42 on the bottom thereof that match the tightening holes 17 in the stem 15. In the top of socket 41 is a square shaped rachet hole 43 into which a ratchet wrench (not shown) is placed. The socket 41 can also be used to remove the stem 15 from the base 10 should replacement be necessary. Another means for installing or removing the replaceable stem 15 is a wrench 44, shown in FIG. 16, which has similarly placed pegs 42 designed to match the stem tightening holes 17.

To utilize the system and to implant the devices of the invention, the following procedure is followed:

1. The patient is anesthetized and the appropriate jig 21 is placed over the gum.
2. Utilizing the gum cutting scalpel 29 the gum is cut along its center line and the gum is peeled away from the maxilla and/or mandible.
3. With the jig 21 still in place, the jig riding guide 36 is attached to the router 35 and the proper sized and shaped router bit 37 is installed so that the procedure of a dado cut groove of the desired depth, can be made into the mandible and/or maxilla.
4. The guide 36 is replaced by the precisely angled guide 39 and, after assuring the installation of the guide is proper, the proper sized straight router bit 38 is attached to the router 35.
5. The first angled flange groove 40 is then cut to the same size and depth as the flange 11 or 12 on the base to be implanted.
6. The angled guide 39 is then rotated 180 degrees on the router 35 so that the router is now set to form the groove for the second flange. The opposite second flange groove is then formed.
7. The base 10 is prepared by inserting the proper stem 15 therein and tightening the stem through the use of the socket 41 with a ratchet wrench (not shown) or the tightening wrench 44.
8. The dado cuts formed in the mandible and/or maxilla are cleaned and the base 10 is inserted therein. Prior to inserting the base 10 it is important to assure that the moveable flange 12 is rotated to the insertion position shown be the dotted lines in FIG. 3. Then as the base 10 is placed into the newly formed groove in the bone, the ridge between the two flange grooves 40 forces the moveable wing flange 12 to open to its implanted position as shown by the solid lines in FIG. 3.

9. After a dental adhesive or epoxy resin has been applied to the post 16 and the straight sided ridge 10a, the properly sized cap, colored to match the natural teeth in the mouth, is properly positioned so that the round post 16 fits into the round hole 16a as shown in FIG. 4, and the rectangular ridge 10a fits into the side view of the rectangular recess 10b as shown in FIG. 4. The method of the straight sided ridge 10a fitting into the perfectly matched recess 10b prevents any sideways motion of the cap 18, and also allowing the bottom of cap 18 to completely rest on the base 10 and the exposed bone alongside the base as shown in FIG. 13.

10. A strip of a biocompatable pliable material 46 is placed around both the front and rear of the teeth so that the material 46 extends from a point above the now restored gum-line to a point over the gum but below the line where the gum had been peeled back on the maxilla and/or mandible bone structure. A biocompatable spring type holding wire 47 is then placed over the pliable holding strip 46 to hold that strip into place. (See FIG. 17.)

The above procedure is then repeated for each tooth to be implanted. It is recognized that various steps in the implantation can be interchanged. For example, it is possible to place the base 10 into the jaw bone prior to screwing in the stem 15. Secondly, if several implants are to be made at one time, the caps 18 can be placed after each base is implanted or all the bases can be implanted first, followed be placement of all the caps. It is also possible to use one continuous base structure or base structures that carry several stems, rather than placing an individual base for each cap. It may also be desireable to implant the base structures 10 and allow some healing and ingrowth of the tissue before the caps are permanently placed.

Or it may be expeditiously possible that in some cases the complete base 10 with the adhered top 18 may be set into the prepared cavity of the mandible and/or maxilla and temporarily wired, as in the present case of some dental bridgework, until the ingrowth of the bone structure holds the implant permanently.

Should it be necessary at some time to remove the cap 18, it may be drilled away. If necessary, the removeable stem 15 can then be extracted by using the wrench 44 or socket 41 and a new stem 15 and cap 18 can be installed.

I claim:

1. An implantable dental prosthesis for permanently mounting into the mouth comprising;
    a stem carrying a post in the top end thereof for permanently mounting an artificial tooth, said stem having a lower threaded portion; and a base having a threaded opening in the top thereof into which the lower threaded portion of the stem is secured, the base further having at least two flanges secured as integral parts of the bottom thereof, one flange is permanently fixed at an angle to the center line of the base and a second flange is rotatable in the opposite direction to a second position at an angle to the center line of the base such that said second flange rotates automatically in an outward direction as the base is positioned into the jaw bone.

2. The prosthesis of claim 1 further comprising an artificial tooth mounted on said stem.

3. The prosthesis of claim 1 wherein the degree of the angle of said second position is substantially the same from the center line of said base as the angle of said fixed flange.

* * * * *